(12) United States Patent
McEwen et al.

(10) Patent No.: US 8,366,740 B2
(45) Date of Patent: Feb. 5, 2013

(54) ULTRASONIC TOURNIQUET SYSTEM

(75) Inventors: James A. McEwen, Vancouver (CA); Michael Jameson, North Vancouver (CA)

(73) Assignee: Abatis Medical Technologies Limited (IE)

( * ) Notice: Subject to any disclaimer, the term of this patent is extended or adjusted under 35 U.S.C. 154(b) by 275 days.

(21) Appl. No.: 12/670,264

(22) PCT Filed: Jul. 23, 2008

(86) PCT No.: PCT/CA2008/001363
§ 371 (c)(1),
(2), (4) Date: Jan. 22, 2010

(87) PCT Pub. No.: WO2009/012594
PCT Pub. Date: Jan. 29, 2009

(65) Prior Publication Data
US 2010/0191277 A1 Jul. 29, 2010

Related U.S. Application Data

(60) Provisional application No. 60/951,632, filed on Jul. 24, 2007.

(51) Int. Cl.
*A61B 17/00* (2006.01)
*A61B 5/02* (2006.01)

(52) U.S. Cl. ........................................ 606/203; 600/499

(58) Field of Classification Search .......... 606/201–203; 600/499
See application file for complete search history.

(56) References Cited

U.S. PATENT DOCUMENTS

| | | | | |
|---|---|---|---|---|
| 5,307,811 A | * | 5/1994 | Sigwart et al. | 600/490 |
| 5,503,156 A | | 4/1996 | Millar | |
| 5,584,853 A | * | 12/1996 | McEwen | 606/201 |
| 5,643,315 A | * | 7/1997 | Daneshvar | 606/201 |
| 2004/0147956 A1 | * | 7/2004 | Hovanes et al. | 606/202 |
| 2010/0022886 A1 | * | 1/2010 | Ayati et al. | 600/454 |

FOREIGN PATENT DOCUMENTS

| | | |
|---|---|---|
| WO | 2005011479 | 2/2005 |
| WO | 2009012594 | 1/2009 |

* cited by examiner

*Primary Examiner* — Katherine Dowe
(74) *Attorney, Agent, or Firm* — Hancock Hughey LLP

(57) ABSTRACT

A system for controlling blood flow through a zone of a patient limb, the zone being bounded by a proximal end and a distal end, comprises: a cuff configured for securing to the limb and for covering the zone, the cuff being inflatable to provide pressure to the zone for occluding the flow of blood flowing through the zone in the direction from the proximal to distal ends of the zone; an array of sensors fitting between the cuff and the limb and arranged for sensing and signaling the amount of penetration of blood flow into the zone; and a control instrument connected to the array and to the cuff for regulating the pressure in the cuff to occlude the blood flow in the zone depending upon the amount of blood flow penetration signaled by the array.

10 Claims, 8 Drawing Sheets

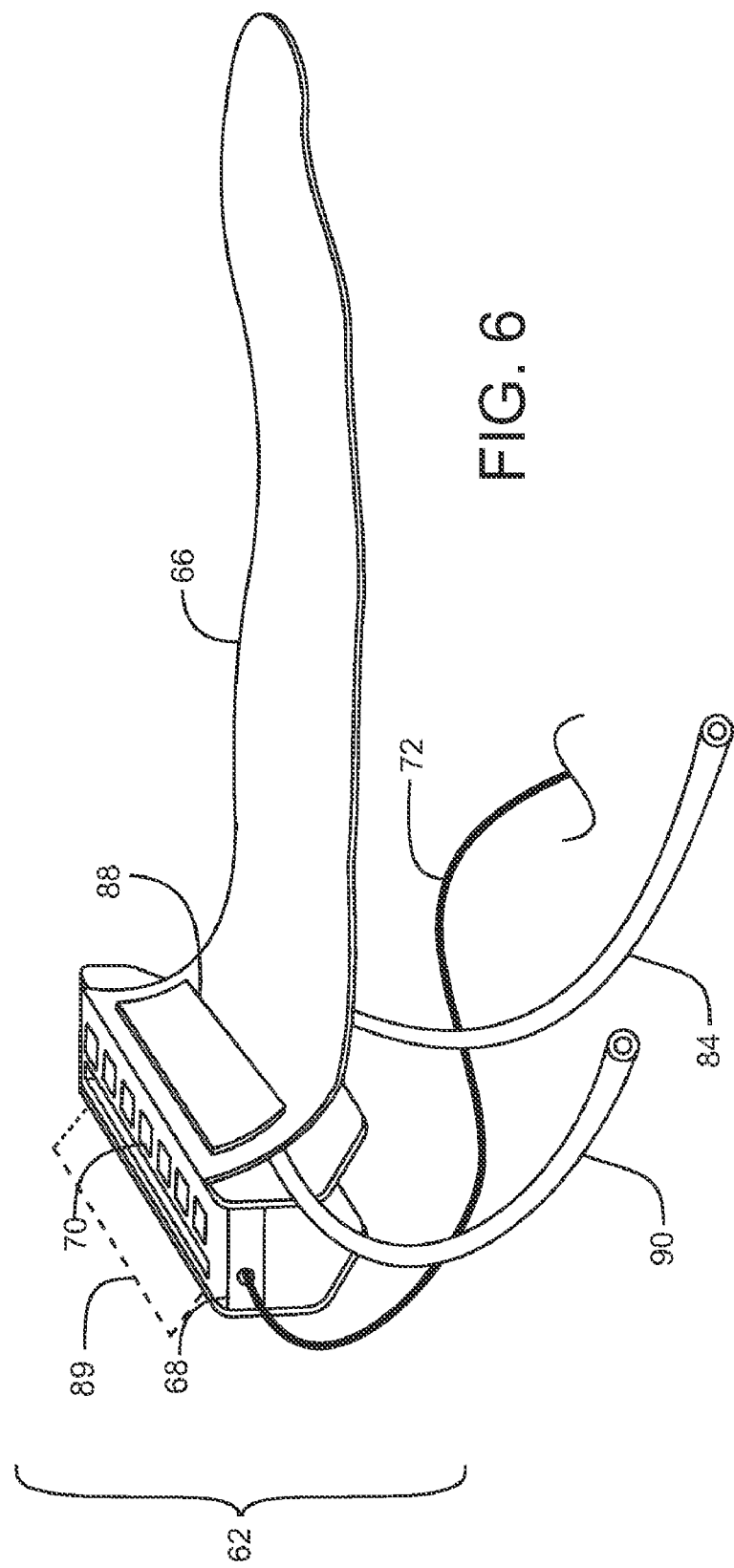

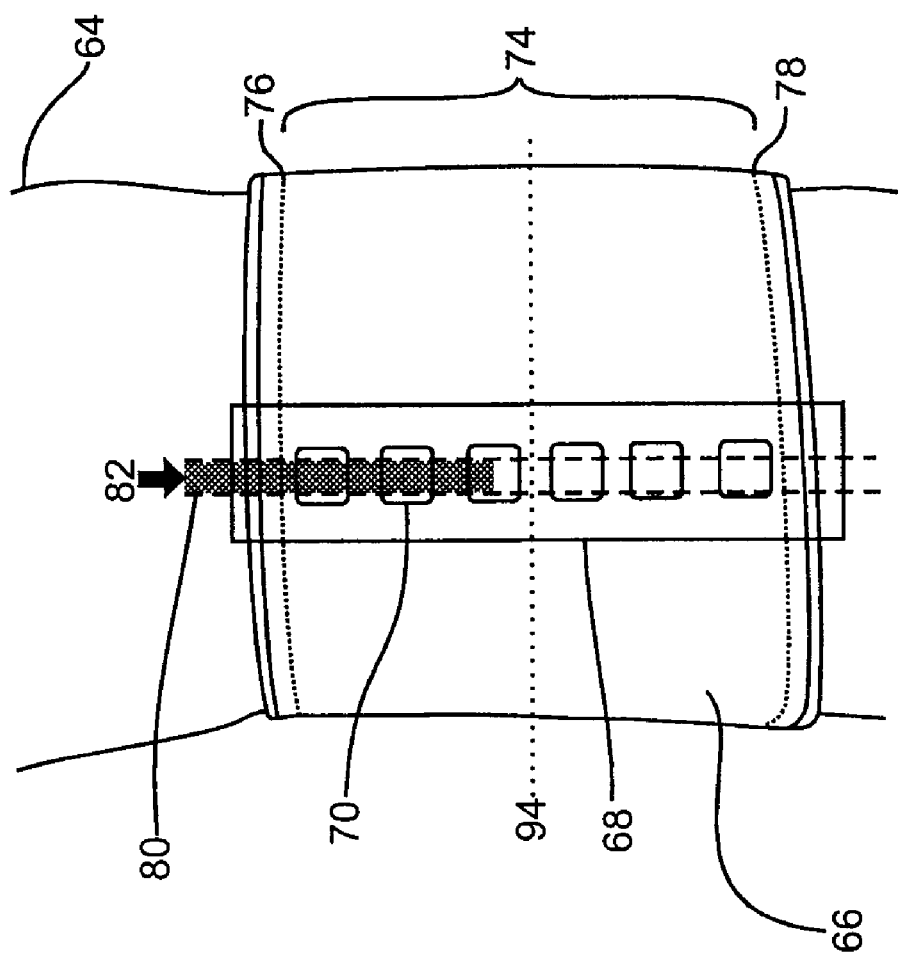

ULTRASONIC TOURNIQUET SYSTEM

FIELD OF THE INVENTION

This invention pertains to tourniquet systems commonly used for stopping arterial blood flow into a portion of a surgical patient's limb to facilitate the performance of a surgical procedure, and for emergency and military applications.

BACKGROUND OF THE INVENTION

Typical surgical tourniquet systems of the prior art include a tourniquet cuff which encircles the limb of a surgical patient and a tourniquet instrument which is releasably connected to an inflatable bladder within the tourniquet cuff through a length of tubing, thereby establishing a gas-tight passageway between the cuff and the tourniquet instrument. The tourniquet instrument contains a pressurized gas source which is used to inflate and regulate the pressure in the tourniquet cuff above a minimum pressure required to stop arterial blood flow distal to the cuff, for a duration suitably long for the performance of a surgical procedure. Many types of surgical tourniquet systems have been described in the prior art, such as those described by McEwen in U.S. Pat. No. 4,469,099, No. 4,479,494, No. 5,439,477 and McEwen and Jameson in U.S. Pat. No. 5,556,415 and No. 5,855,589.

Many studies published in the surgical literature have shown that the safest tourniquet pressure is the lowest pressure that will stop the flow of arterial blood past a specific cuff applied to a specific patient for the duration of that patient's surgery. Such studies have shown that higher tourniquet pressures are associated with higher risks of tourniquet-related injuries to the patient. Therefore, when a tourniquet is used in surgery, surgical staff generally try to use the lowest tourniquet pressure that in their judgment is safely possible. It is well established in the medical literature that the optimal guideline for setting the pressure of a constant-pressure tourniquet is based on "Limb Occlusion Pressure" (LOP). LOP can be defined as the minimum pressure required, at a specific time in a specific tourniquet cuff applied to a specific patient's limb at a specific location, to stop the flow of arterial blood into the limb distal to the cuff. The currently established guideline for setting tourniquet pressure based on LOP is that an additional safety margin of pressure is added to the measured LOP, to account for physiologic variations and other changes that may be anticipated to occur normally over the duration of a surgical procedure. Surgical tourniquet systems of the prior art that can automatically measure the LOP of individual surgical patients and that can automatically recommend a tourniquet pressure setting based on measured LOP are described by McEwen in U.S. Pat. No. 5,439,477, by McEwen and Jameson in U.S. Pat. No. 5,556,415, and by McEwen et al. in U.S. Pat. App. No. 20060253150.

Standard cylindrical tourniquet cuffs are ideally suited for application to patients with cylindrical limbs. However, when applied to a patient with a tapered limb, a cylindrical cuff will not optimally match the limb taper, and will typically result in a snug fit proximally and a loose fit distally. Consequently, a cylindrical cuff may prove unable to achieve a bloodless field distal to the cuff at normal pressures or may require a substantially higher and more hazardous inflation pressure to achieve a bloodless field, and when inflated may have a tendency to roll or slide distally on the limb during a surgical procedure. In an effort to match the taper of a patient's limb at a desired cuff location, some tourniquet cuffs of the prior art are designed to have an arcuate shape, and are commonly called contour cuffs. When a contour cuff surrounds a limb having a matching taper, a uniformly snug fit can be achieved between the cuff and the limb from the proximal to distal cuff edges. Wide contour tourniquet cuffs of the prior art have been shown in the surgical literature to substantially reduce pressures required to create a bloodless surgical field distal to the inflated cuff (Younger et al., 'Wide Contoured Thigh Cuffs and Automated Limb Occlusion Measurement Allow Lower Tourniquet Pressures', Clin Orthop 428:286-293, 2004). Lower tourniquet pressures are associated in the surgical literature with lower risk of injuries to surgical patients.

In military combat and emergency situations, loss of blood is a major cause of death if the injured person is alone or when medical assistance is not immediately available. The use of a tourniquet to stop blood loss from an injured arm or leg is a well-known technique for preventing death in these situations. Once the primary objective of preventing death due to blood loss is achieved, it is desirable to prevent further injury to the limb due to excessive pressure and time of tourniquet application. To minimize mechanical injury to the blood vessels and other soft tissues beneath the tourniquet, the pressure applied by the tourniquet to the underlying arterial blood vessels should be only slightly higher than the minimum pressure required to stop blood flow in the vessels. A prior-art tourniquet that has been widely used in military and emergency applications is described by McEwen et al. in U.S. Pat. No. 6,746,470.

There is a need for a tourniquet system that can accurately and reliably sense arterial blood flow in a limb near a tourniquet cuff that encircles the limb. This needed tourniquet system would allow blood flow near the tourniquet cuff to be sensed and continuously monitored so that cuff pressure could be maintained near the minimum pressure required to stop blood flow past the cuff, thus increasing safety in surgery and for emergency and military applications.

There is a related need for a tourniquet system that can apply a selected pressure to a selected portion of a limb beneath a tourniquet cuff in response to blood flow sensed in the portion of the limb. This needed system would allow the application of a level of pressure to the selected portion that is sufficient to stop blood flow in the selected portion without requiring the application of the same level of pressure to other portions of the limb beneath the tourniquet cuff, thereby increasing the precision of pressure application and improving safety.

BRIEF DESCRIPTION OF THE DRAWINGS

FIG. 6 depicts the cuff portion of the alternate embodiment.

FIG. 7 depicts detection of blood flow by the alternate embodiment.

DETAILED DESCRIPTION OF THE PREFERRED EMBODIMENT

The embodiment illustrated is not intended to be exhaustive or limit the invention to the precise form disclosed. It is chosen and described in order to explain the principles of the invention and its application and practical use, and thereby enable others skilled in the art to utilize the invention.

Figure 1:
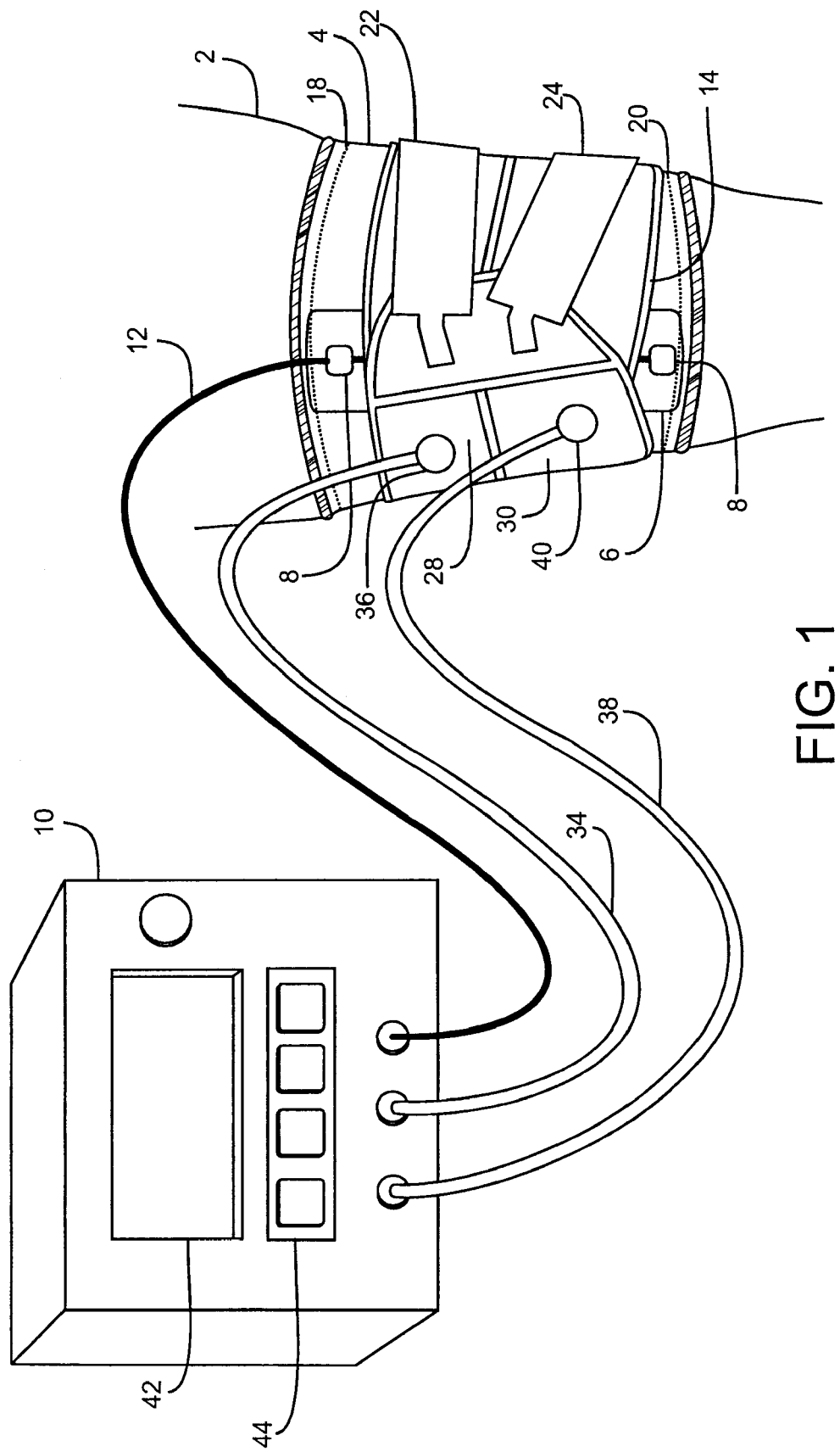
FIG. 1 is a pictorial representation of the preferred embodiment in a surgical application.
Figure 2:
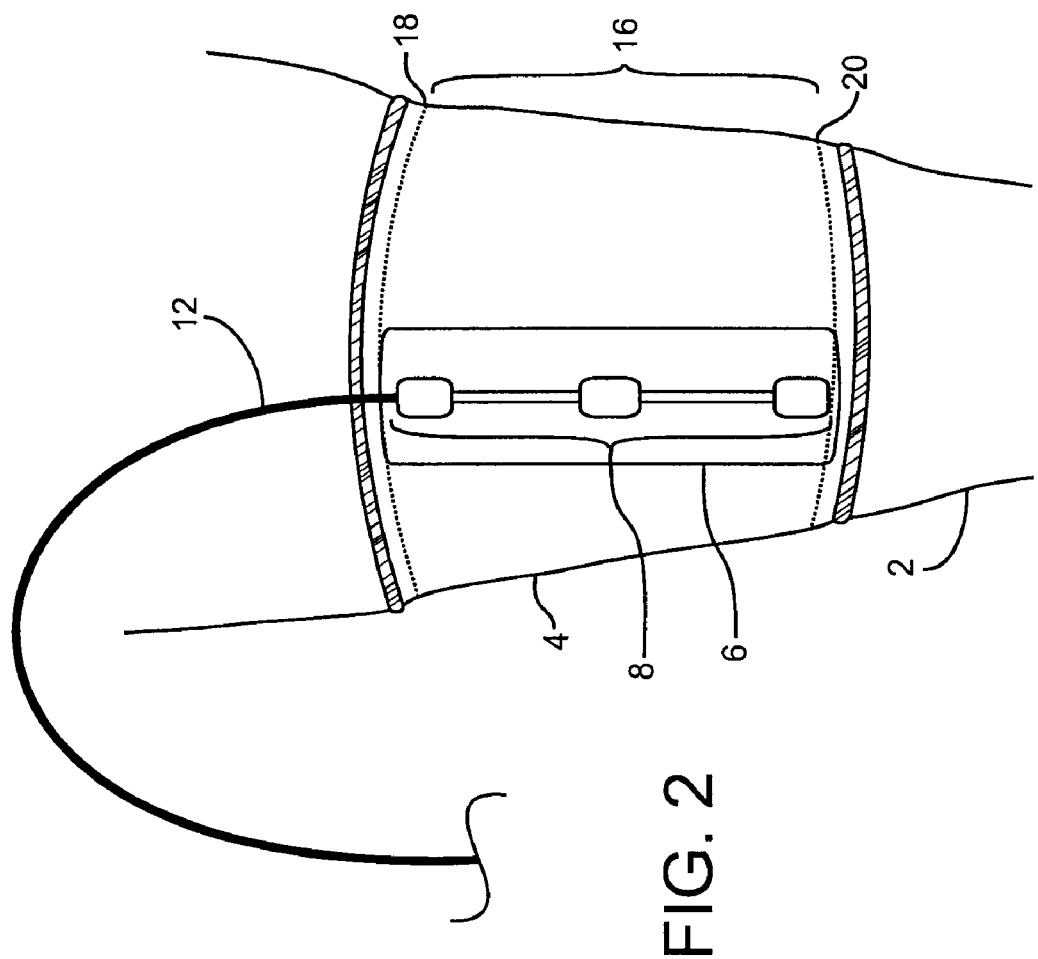
FIG. 2 shows the stretchable sleeve of the preferred embodiment.

FIG. 1 depicts the preferred embodiment in use applied to limb 2 of a patient. Stretchable sleeve 4 is shown applied along a portion of the length of limb 2. Gel pad 6 forms part of sleeve 4 and provides a means for the efficient coupling of high-frequency acoustic energy between ultrasonic transducer array 8 and the tissues of limb 2. Ultrasonic transducer array 8 is connected to instrument 10 via cable 12. Contour tourniquet cuff 14 is applied over sleeve 4 and transducer array 8 to encircle limb 2 at a location desired by a user. This configuration permits ultrasonic transducer array 8 to insonify a volume of tissue within a zone 16 of limb 2 bounded by a proximal end 18 and a distal end 20, as shown in FIGS. 1 and 2, thereby permitting instrument 10 to measure the flow of blood in arteries within zone 16 via the Doppler effect and to detect changes in blood flow that may occur in response to the pressurization of contour cuff 14. As described further below instrument 10 may be configured to control the pressures applied by contour cuff 14 to limb 2 to maintain the blood flow in the insonified arteries at predetermined levels or at levels set by a user of instrument 10.

Ultrasonic transducer array 8 comprises one or more arrays of piezoelectric crystal elements or capacitance micromachined ultrasonic transducer cells or other materials and technologies known in the art to be suitable for transmitting and receiving high frequency acoustic energy. By adjusting the relative phases of electronic signals applied to the crystal elements that comprise an array the ultrasound waves produced by the array may be steered and focused to insonify a selected region within zone 16. Instrument 10 operates ultrasonic transducer array 8 to scan volumes of tissue to detect arterial blood flow. Ultrasonic waves are emitted by transducer 8 at scanning angles relative to the surface of transducer 8 and traverse the tissue underlying transducer 8. The waves emitted by transducer 8 reflect off various tissue structures within the limb. Doppler frequency shifts in the reflections indicate moving structures, such as flowing blood. Regions where blood flow is detected may be localized in terms and scan angle and tissue depth and quantified by analyzing the magnitude of the Doppler frequency shifts of the returned echoes.

FIG. 2 depicts stretchable sleeve 4 of the preferred embodiment applied to limb 2. Sleeve 4 has a tubular and elastically stretchable shape and is designed for use with tourniquet contour cuff 14 and to conform to limbs of varying tapers. Gel pad 6 forms part of sleeve 4 and is comprised of ultrasound coupling gel contained within a thin polyurethane membrane or other material transparent to ultrasound. Gel pad 6 may also be comprised of other conformable materials or substances suitable for coupling ultrasonic transducer 8 to limb 2. In the preferred embodiment, ultrasonic transducer array 8 forms part of gel pad 6; however, it will be apparent however that ultrasonic transducer array 8 could be independent of gel pad 6 and interposed between contour cuff 14 and gel pad 6 of sleeve 4. For clarity only a single gel pad 6 and transducer array 8 have been shown and described; however, it will be apparent that sleeve 4 may contain multiple gel pads with transducer arrays spaced circumferentially around the sleeve and that sleeve 4 could be formed entirely of a stretchable ultrasound conducting substance or materials. Sleeve 4 may include one or more gel pads suitable for the coupling of high-frequency acoustic energy between the tissues of limb 2 and ultrasonic transducer array 8. Sleeve 4 has a tubular and elastically stretchable shape, with an un-stretched circumference of less than the minimum limb circumference recommended for contour cuff 14 so that it may be elastically stretched when applied to a limb having the minimum recommended circumference. Sleeve 4 may be elastically stretched in a radial direction to a circumference at least equal to the maximum limb circumference recommended for contour cuff 14. When elastically stretched and applied to a limb having the maximum recommended circumference, the maximum pressure applied to the underlying limb by sleeve 4 may be less than the pressure required to occlude venous blood flow in the limb. When applied to a limb having the maximum recommended circumference, the length of the gel pad within sleeve 4 is not less than width of contour cuff 14. When elastically stretched and applied to a limb having the minimum recommended circumference, the pressure applied to the underlying limb by sleeve 4 is sufficient to maintain sleeve 4 and gel pad 6 in full contact with the limb throughout the length of sleeve 4 and gel pad 6.

Figure 3:
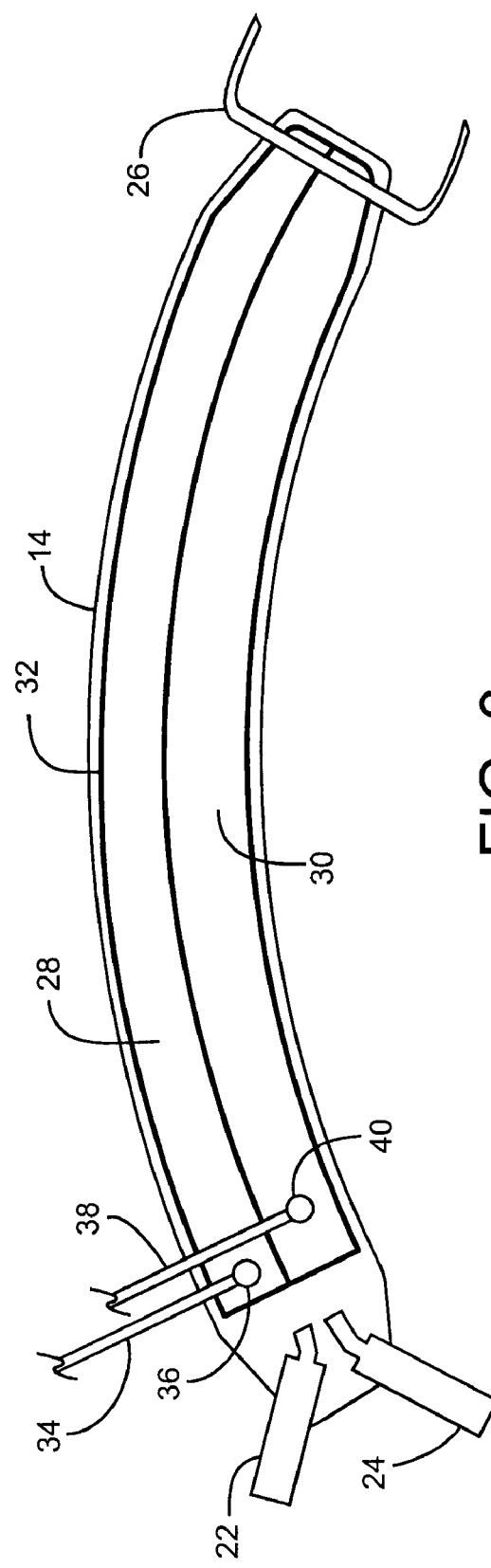
FIG. 3 depicts the contour cuff portion of the preferred embodiment.

Contour cuff 14 is similar in design and construction to the cuff described by McEwen et al. in U.S. patent application Ser. No. 11/384,695. As shown in FIG. 3 contour cuff 14 has a substantially arcuate shape with the width of the cuff reduced near the end edges. The arcuate shape of cuff 14 and the degree to which the width near the end edges is reduced are predetermined to allow cuff 14 to be applied to limbs with a predetermined range of tapers such that contour cuff 14 remains substantially in contact with the limb along its width around the circumference of the limb. When contour cuff 14 is correctly applied to a patient limb as shown in FIG. 1 the side edge of contour cuff 14 with the greater radius is proximal and the side edge with the lesser radius is distal on the limb.

Contour cuff 14 is secured around the limb by securing straps 22 and 24. Securing straps 22 and 24 are non-releasably attached to a non-inflating region of contour cuff 14 near an end edge. Securing straps 22 and 24 have fastening portions which releasably engage with the outer surface of cuff 14 and bending portions which permit the fastening portions to be positioned such that they can completely engage the outer surface within the side edges of contour cuff 14. In the preferred embodiment the outer surface of contour cuff 14 and the fastening portions of securing straps 22 and 24 are formed from Velcro-type materials. The outer surface of cuff 14 is a loop type material and the fastening portions of securing straps 16 and 18 are formed from hook type material. Tie strap 26 shown in FIG. 3, provides a means for the user to align and pull cuff 14 snug around limb 2. When contour cuff 14 has been secured around limb 2 the ends of tie strap 26 may be tied together to help maintain the overlapping portion of the cuff in alignment around limb 2 by preventing the cuff from twisting, telescoping and rolling on the limb when pressurized. For clarity, tie strap 26 is not shown in FIG. 1.

Contour cuff 14 has two independent cuff bladders, proximal cuff bladder 28 and distal cuff bladder 30; the perimeter 32 of the bladders is depicted in the top view of contour cuff 14 shown in FIG. 3. The proximal and distal cuff bladders are pressurized with fluid from instrument 10 to apply pressure to proximal and distal portions of limb 2 underlying cuff 14. In the preferred embodiment the fluid used to pressurize (inflate) the cuff bladders of contour cuff 14 is air, it will be apparent that other fluids could be used, for example the fluid could be another gas such as nitrogen or the fluid could a liquid such as water. Air from instrument 10 is supplied to proximal bladder 28 via tubing 34 and bladder port 36, fluid is supplied to distal bladder 30 via tubing 38 and bladder port 40. Contour cuff 14 is known in the art as single port cuff, it will be apparent that cuff 14 could be configured as a dual port and instrument 10 adapted with separate connections to each bladder for the supply of fluid to the bladder and the measurement of pressure within the bladder.

As can be seen in FIG. 1, instrument 10 has a user interface consisting of graphic display panel 42 and keypad 44. Display panel 42 is employed for the selective display of information in alphanumeric and graphical formats that may include: measured pressure levels in proximal bladder 28 and distal bladder 30, reference or desired pressure levels in proximal bladder 28 and distal bladder 30, blood flow measurements from transducer 8, and other information required for the operation of instrument 10.

Keypad 44 provides a means for a user of instrument 10 to control the operation of instrument 10.

Figure 4:
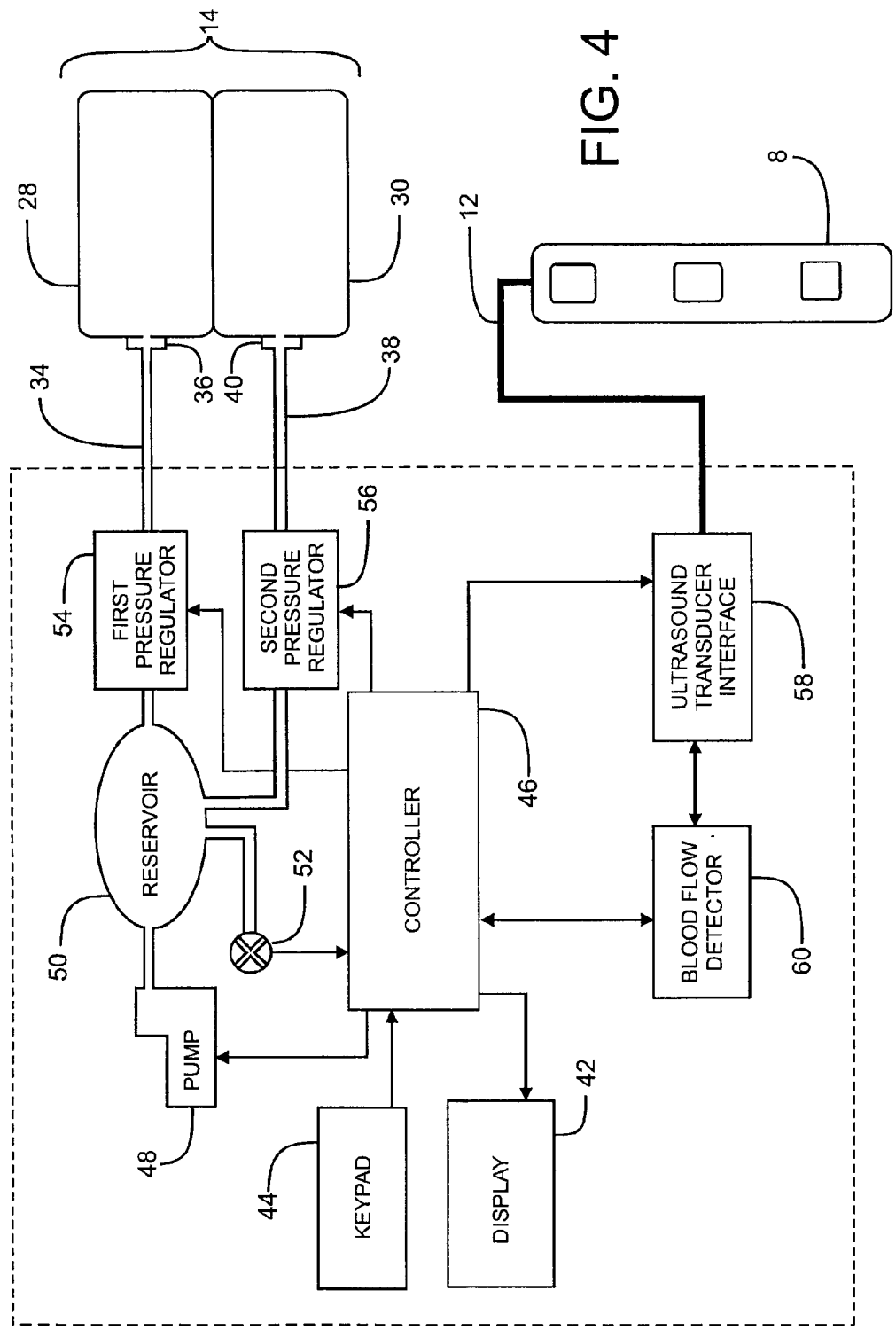
FIG. 4 is a block diagram of the instrument portion of the preferred embodiment.

Referring to the block diagram of instrument 10 shown in FIG. 4, controller 46 comprises a microcomputer, associated memory and control software, analog and digital peripheral interface circuitry, and other necessary support components for the operation of instrument 10.

As shown in FIG. 4, pneumatic pump 48 is pneumatically connected to reservoir 50. In response to control signals from controller 46, pump 48 operates to pressurize reservoir 50. Reservoir pressure transducer 52 is pneumatically connected to reservoir 50 and generates a reservoir pressure signal. The reservoir pressure signal is communicated to controller 46. Controller 46 acts to maintain the pressure in reservoir 50 near a predetermined or calculated reservoir pressure level.

Instrument 10 is shown configured with two pressure regulators, first pressure regulator 54 and second pressure regulator 56. First pressure regulator 56 maintains the pressure in proximal cuff bladder 28 near the level of the first cuff pressure reference level communicated from controller 46. Second pressure regulator 56 maintains the pressure in distal cuff bladder 30 near the level of the second cuff pressure reference level communicated from controller 46. Although instrument 10 has been described with two pressure regulators it will be apparent that additional pressure regulators could be included within instrument 10 to independently control the pressure in multiple cuff bladders to apply differing selected pressures to various selected portions of a limb.

Ultrasonic transducer interface 58 is the ultrasound engine of instrument 10 and includes transceivers for driving and receiving signals from the elements of transducer array 8 and electronics for beam forming, steering, focusing, signal amplification, filtering, and signal processing functions. Interface 58, under the direction of control of signals from controller 46, acts to scan volumes of tissue within zone 16 to produce signals indicative of blood flow for communication to blood flow detection module 60.

Blood flow detection module 60 receives signals from ultrasonic transducer interface 58 indicative of scan position and Doppler blood flow magnitudes. The module uses this information to detect the volumes of tissue within the scanning area of transducer 8 where blood flow is present and to quantify and localize the blood flow information for communication to controller 46 and display to a user.

Signals from blood flow detection module 60 may be used by controller 46 to perform automatic measurements of limb occlusion pressure (LOP). LOP is the minimum pressure required, at a specific time in a specific tourniquet cuff applied to a specific patient's limb at a specific location, to stop the flow of arterial blood into the limb distal to the cuff. Controller 46 of instrument 10, in response to user input via keypad 44, may measure LOP by: first automatically scanning for arterial blood flow in the tissue of limb 2 immediately distal to contour cuff 14, then after localizing and quantifying the blood flow automatically increasing the second cuff reference pressure level to increase the pressure applied by distal cuff bladder 30 to the tissues of limb 2 until the blood flow detected distal to contour cuff 14 falls below a predetermined minimum flow threshold, or until the pressure in distal cuff bladder exceeds a predetermined maximum bladder pressure. The pressure level within bladder 30 at which the detected blood flow distal to the contour cuff 14 first falls below the predetermined minimum flow threshold is the measured LOP for distal bladder 30. Controller 46 can act similarly to determine the minimum pressure required in proximal cuff bladder 28 to prevent blood flow past bladder 28.

A measurement of LOP as described above is valid only at the time the measurement is made, and physiological parameters that change over time such as blood pressure may cause changes in LOP over time. To automatically maintain the minimum pressures required in proximal bladder 28 and distal bladder 30 to prevent blood flow past cuff 14 over a period of time when physiologic parameters may vary, such as during a time period suitably long for surgery, instrument 10 operates as follows: a) first the LOP for proximal bladder 28 and distal bladder 30 is automatically determined, as described above, and the bladders are pressurized by setting the first and second reference pressure levels to the respective LOP values measured for each cuff bladder; b) the limb tissues insonified by ultrasonic transducer 8 are continuously scanned to localize and quantify blood flow within zone 16 which includes tissue volumes proximal and distal and beneath contour cuff 14; c) controller 46 continuously measures the LOP of proximal bladder 28 by first decreasing the first reference pressure level until the detected blood flow past proximal bladder 28 is above a predetermined flow threshold and then increasing the first reference pressure level until detected blood past proximal bladder 28 is below a predetermined flow threshold; d) the second reference pressure level, and thereby the pressure applied to limb 2 by distal cuff bladder 30, is automatically adjusted to reflect any change in the value of LOP measured for proximal bladder 28 (for example, if the minimum pressure required to occlude blood flow past proximal bladder 28 decreases by 15 mmHg then the pressure applied by distal bladder 30 is reduced by 15 mmHg, and conversely if the pressure required to occlude blood flow past proximal bladder 28 increases by 15 mmHg then the pressure applied by distal bladder 30 is increased by 15 mmHg); and e) if at any time blood flow is detected distal to cuff 14 then controller 46 may incrementally increase the pressure level in distal bladder 30 by predetermined amounts until the detected flow stops.

In another mode of operation, instrument 10 may operate to continuously maintain the minimum pressures necessary to occlude blood flow distally past contour cuff 14. This is accomplished by first automatically increasing the pressure applied by distal bladder 30 and proximal bladder 28 until blood flow sensed beneath the cuff is less than a predetermined minimum. Then, pressure is continuously varied by incrementally increasing and decreasing the pressure applied by proximal bladder 28 to maintain the rate of blood flow sensed beneath contour cuff 14 below and near the predetermined minimum threshold. In this mode of operation, the pressure in distal bladder 30 is automatically adjusted to reflect any change in the pressure required in the proximal bladder 28 to occlude blood flow beneath contour cuff 14.

Figure 5:
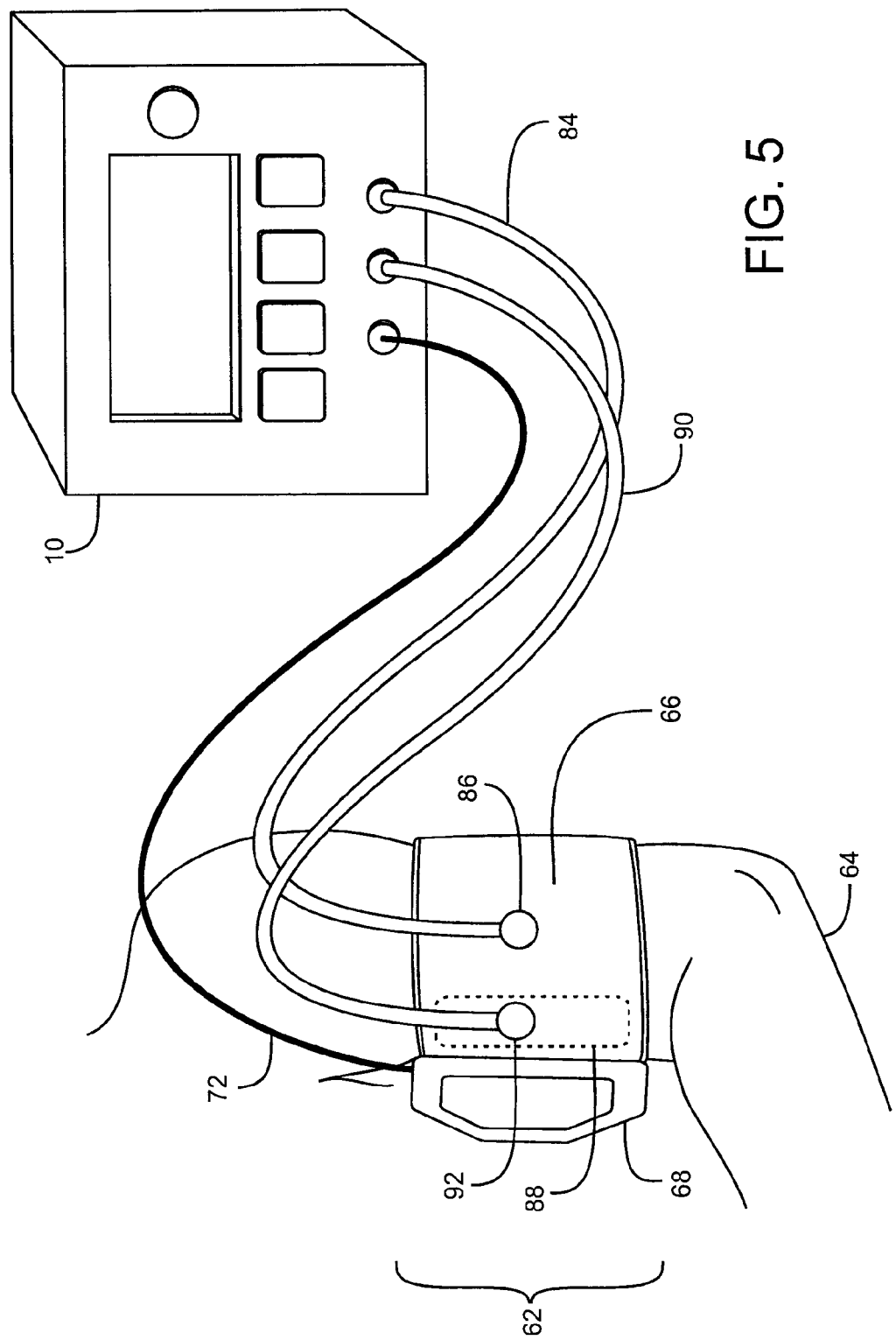
FIG. 5 is alternate form of the preferred embodiment.

FIGS. 5, 6, 7, 8a and 8b depict an alternate embodiment of the invention. In FIG. 5 emergency and military tourniquet (EMT) cuff 62 is shown applied to patient limb 64. EMT cuff 62 is similar in design and construction to the cuff described in U.S. Pat. No. 6,746,470 and is adapted for rapid application to a limb in an emergency or life threatening situation such as military combat. Bladder 66 is fixed at one end to EMT cuff clamp 68. To apply cuff 56 to a limb bladder 66 encircles the limb and the free end of bladder 66 passes through the sealing surfaces of EMT cuff clamp 68. EMT cuff clamp 68 retains cuff bladder 66 around limb 64 and seals the encircling bladder 66 across its width. The width of the sealing surfaces of clamp 68 are selected to be greater than the width of bladder 66 thereby allowing bladder 66 to be sealed across its width at angles other than 90 degrees relative to the bladder edge, such as is the case when bladder 66 assumes a conical shape when wrapped around a conical limb (such as a typical thigh). This is important in achieving a snug fit around limbs of various degrees of conical shape.

The limb facing surface of EMT cuff clamp 68 includes ultrasonic transducer array 70 which communicates with instrument 10 via cable 72. Ultrasonic transducer array 70 is similar to transducer array 8 described above and is shown in FIGS. 6 and 7. Ultrasound coupling gel or a gel pad may be placed between the face of ultrasonic transducer array 70 and limb 64.

EMT cuff 62 is preferably applied to a limb such that clamp 68 with transducer array 70 is positioned over the major artery in the limb, for example when applied to the upper arm the camp is placed over the brachial artery or when applied to the upper thigh the clamp is placed over femoral artery. As shown in FIG. 7 ultrasonic transducer array 70 insonifies a volume of tissue within zone 74 of limb 64. Zone 74 is bounded by a proximal end 76 and a distal end 78. Ultrasound transducer array 70 is used to measure blood flow in the portion of major artery 80 that lies within zone 74. Changes in blood flow in major artery 80 in response to pressures applied to the limb by EMT cuff 62 can be detected by ultrasound transducer array 70. In FIG. 7 the direction of blood flow 82 in the major artery 80 is shown and the shaded area of major artery 80 represents penetration of blood flow beneath EMT cuff 62.

Encircling cuff bladder 66 is pressurized by first pressure regulator 54 of instrument 10 via tubing 84 and bladder port 86. As shown in FIGS. 5, 6, 8a and 8b EMT cuff 62 includes an auxiliary bladder 88 which is located on the limb facing surface of encircling bladder 66. Auxiliary bladder 88 is pressurized by second pressure regulator 56 of instrument 2 via tubing 90 and bladder port 92. In the preferred embodiment the width of auxiliary bladder 88 is no greater than the width of encircling bladder 66 and the length of auxiliary bladder is less than the inflating portion of encircling bladder 66 when secured around a limb by clamp 68. Auxiliary bladder 88 is pressurized by instrument 10 to extend the reach of encircling bladder 66 in a predetermined location to occlude blood flow, as detected by ultrasonic transducer array 70, in arteries lying deep within the tissues of limb 64 (within a portion of zone 74) underlying auxiliary bladder 88. This configuration of overlapping cuff bladders allows for the selective application of pressure to occlude deep arteries without increasing the overall pressure applied to the limb. It will be appreciated that to apply additional or supplemental pressure to other portions of limb 64 encircled by EMT cuff 62 additional auxiliary bladders of varying shape and size may be selected to form part of EMT cuff 62, and that these bladders may not necessarily overlap with encircling bladder 66.

The invention may automatically maintain the pressures applied to a limb by EMT cuff 62 at the minimum level required to prevent blood flow distal to the location of the cuff on the limb. Typically, a user first applies ultrasound coupling gel or a gel pad to the transducer surfaces of EMT clamp 68. Next, EMT cuff 62 is applied to a limb 64 at a desired location by wrapping encircling bladder 66 around the limb at the location; the end of bladder 66 is pulled through clamp 68; clamp 68 is approximately aligned above the major limb artery 80; and clamp 68 is secured to maintain bladder 66 snugly around the limb and clamp 68 in contact with the tissues of limb.

Instrument 10 is then directed via keypad 44 to automatically scan for arterial blood flow in the limb tissues underlying clamp 68 and to increase the pressure in encircling bladder 66 until a predetermined pressure threshold is reached or until the rate of blood flow distal to the midline 94 of EMT cuff 56 is equal to or less than a predetermined minimum flow threshold. If the predetermined pressure threshold is reached in encircling bladder 66 and blood flow distal to the midline of EMT cuff 62 remains above the predetermined minimum flow threshold, instrument 10 may act to pressurize auxiliary bladder 88 to occlude arteries lying deeper beneath EMT cuff 62. To maintain the pressure in encircling bladder 66 and auxiliary bladder 88 at the minimum necessary to prevent blood flow distal to EMT cuff 62, instrument 10 continues to monitor blood flow in limb tissues proximal to the midline 94 of EMT cuff. Instrument 10 continues to scan for arterial blood flow in tissues underlying clamp 68 and monitors the distance that blood flow penetrates beneath the cuff from the proximal edge towards the midline. Instrument 10 automatically adjusts the pressure within bladders 66 and 88 within predetermined limits to prevent blood flow from penetrating beyond the midline 94 of EMT cuff 62, thereby maintaining the pressures in EMT cuff 62 at the lowest level necessary to occlude blood flow past EMT cuff 62.

It will be apparent that instrument 10 may be used to monitor blood flow beneath a cuff, and generate alarms perceivable by a user if the blood flow sensed beneath the cuff exceeds a predetermined penetration threshold. For example, an alarm may be generated if the sensed blood flow past the midline of the cuff exceeds a predetermined threshold, or an alarm may be generated to indicate that sensed blood flow beneath the cuff is nearing the midline of the cuff and thus alert the user to the possibility that blood flow past the cuff may be imminent. These alarms may be operable regardless of whether the cuff pressure level was established automatically as described above, or was established by user input to instrument 10, or was established manually by application of the cuff in an emergency or military setting.

Figure 8B:
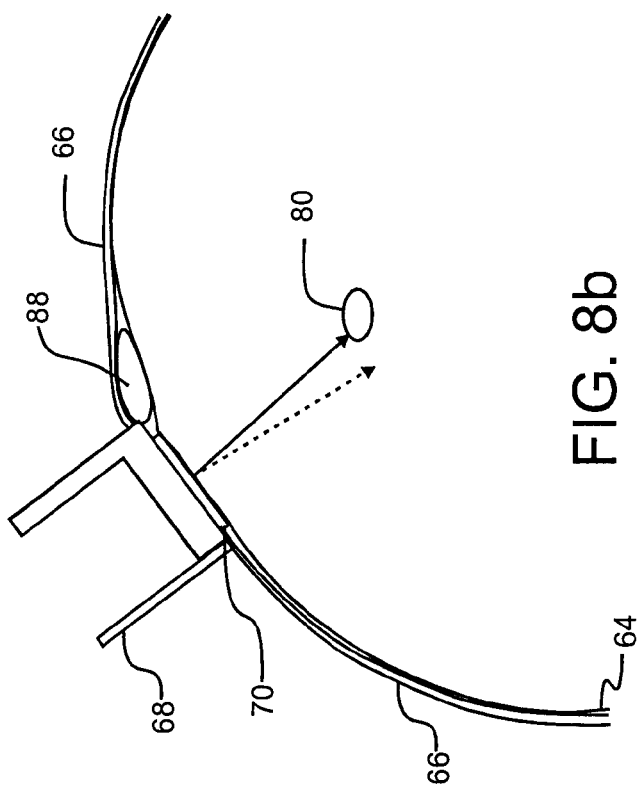
FIGS. 8a and 8b depict the operation of an auxiliary bladder of the alternate embodiment.
Figure 8A:
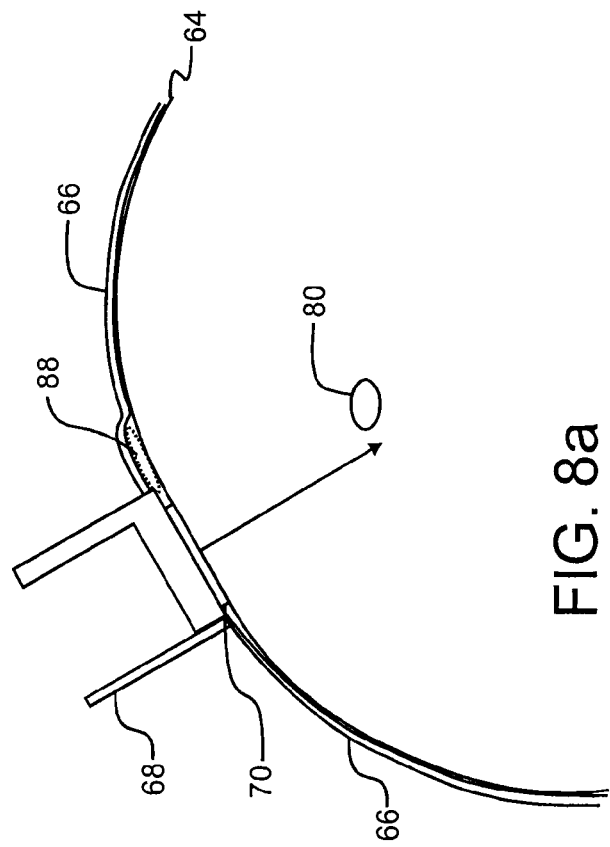

Auxiliary bladder 88 of EMT cuff 62 may be adapted as described above to provide EMT cuff 62 with additional reach in a selected area or may be adapted as described below and shown in FIGS. 8a and 8b to extend the volume of tissue that may be scanned by transducer array 70. The maximum volume of tissue that can be insonified by transducer array 70 to detect blood flow is determined by the geometry and other physical and electrical characteristics of transducer array 70. The face of clamp 68 containing transducer array 70 is normally tangent to the surface of limb 64. By varying the angle of the face of transducer array 70 with respect to the surface of the limb additional tissue volumes may be scanned for blood flow. This would be much like a user varying the angle a hand held ultrasound probe held parallel to the limb to search for arterial blood flow. Auxiliary bladder 88 may be positioned close to clamp 68 and act as a "transducer scanning" bladder so that when it is pressurized to a pressure above that of encircling bladder 66 it will inflate against the limb and cause clamp 68 to tilt relative to the limb surface as shown in FIG. 8b. Instrument 10, by varying the pressure within auxiliary bladder 88, can mechanically scan ultrasonic transducer array 70 to extend the volume of tissue in which blood can be detected. This simple low-cost mechanical scanning of ultrasonic transducer array 70 may permit greater tolerance in the application of clamp 68 to the limb with respect to the position of the clamp relative to the major arteries of the limb. It will be apparent that additional auxiliary transducer scanning bladders (as shown, for example, in dashed lines at 89, FIG. 6) may form part of cuff 62 to provide mechanical scanning in more than one direction and that scanning bladders may form part of contour cuff 14 described above, and be configured to control the angle of the face of ultrasonic transducer 8 with respect to limb 2.

We claim:

1. A system for controlling blood flow through a zone of a patient limb, the zone being bounded by a proximal end and a distal end, comprising:
    a cuff configured for securing to the limb and for covering the zone, the cuff being inflatable to provide pressure to the zone for occluding the flow of blood flowing through the zone in the direction from the proximal to distal ends of the zone;
    an array of sensors fitting between the cuff and the limb and arranged for sensing and signaling a distance from the proximal end that the arterial blood flow penetrates into the zone; and
    a control instrument connected to the array and to the cuff for regulating the pressure in the cuff to occlude the blood flow in the zone depending upon the arterial blood flow penetration distance signaled by the array; and
    an inflatable auxiliary bladder disposed adjacent to the array and inflatable independently from the cuff for varying an angular position of the sensors of the array relative to the limb while the zone is covered with the inflatable cuff secured to the limb to provide pressure to the zone, thereby to scan various tissue volumes.

2. The system of claim 1 wherein the instrument establishes a threshold penetration of blood flow and is operable for occluding blood flow in the zone when the arterial blood flow penetration distance signaled by the array exceeds that threshold.

3. The system of claim 2 wherein the threshold is established to be the midline between the proximal and distal ends.

4. The system of claim 1 further comprising a clamp to which the array is mounted, the clamp also configured for securing the cuff in position on the limb for covering the zone.

5. The system of claim 1 further comprising an inflatable auxiliary bladder disposed adjacent to the cuff and separately operable by the control instrument to supplement the pressure applied to a portion of the zone by the cuff.

6. A method of controlling blood flow through a zone of a patient limb, the zone being bounded by a proximal end and distal end, comprising the steps of:
    covering the zone with an inflatable cuff secured to the limb to provide pressure to the zone for occluding the flow of blood flowing through the zone in the direction from the proximal to the distal ends of the zone;
    sensing and signaling a distance of penetration of arterial blood flow into the zone from the proximal end; and
    regulating the pressure in the cuff to occlude the blood flow in the zone depending upon the distance signaled; and
    wherein the sensing and signaling step includes varying a sensing angle of sensors relative to the limb while the zone is covered with the inflatable cuff secured to the limb to provide pressure to the zone, thereby to scan various tissue volumes.

7. The method of claim 6 including the steps of:
    establishing a threshold penetration of blood flow; and
    occluding blood flow in the zone when the arterial blood flow penetration distance signaled exceeds that threshold.

8. The method of claim 7 including the step of establishing the threshold to be the midline between the proximal and distal ends.

9. The method of claim 6 including the step of:
    mounting to a clamp sensors for sensing and signaling the distance of penetration of arterial blood flow into the zone from the proximal end; and
    using the clamp to secure the cuff to the limb.

10. The method of claim 6 including the step of pressuring a portion of the zone to supplement the pressure provided by the cuff to the zone.

* * * * *